United States Patent
Kawano et al.

(10) Patent No.: US 9,205,414 B2
(45) Date of Patent: Dec. 8, 2015

(54) CATALYST FOR PRODUCING UNSATURATED ALDEHYDE AND/OR UNSATURATED CARBOXYLIC ACID, AND PROCESS FOR PRODUCING UNSATURATED ALDEHYDE AND/OR UNSATURATED CARBOXYLIC ACID USING THE CATALYST

(75) Inventors: Tomoatsu Kawano, Himeji (JP); Yutaka Takahashi, Himeji (JP); Naohiro Fukumoto, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 167 days.

(21) Appl. No.: 13/821,413

(22) PCT Filed: Sep. 7, 2011

(86) PCT No.: PCT/JP2011/070348
§ 371 (c)(1),
(2), (4) Date: Mar. 7, 2013

(87) PCT Pub. No.: WO2012/036038
PCT Pub. Date: Mar. 22, 2012

(65) Prior Publication Data
US 2013/0172615 A1 Jul. 4, 2013

(30) Foreign Application Priority Data

Sep. 17, 2010 (JP) ................................. 2010-208751

(51) Int. Cl.
| | | |
|---|---|---|
| *B01J 27/192* | (2006.01) | |
| *B01J 23/00* | (2006.01) | |
| *B01J 27/228* | (2006.01) | |
| *B01J 23/887* | (2006.01) | |
| *B01J 35/02* | (2006.01) | |
| *B01J 35/06* | (2006.01) | |
| *B01J 37/00* | (2006.01) | |
| *B01J 37/03* | (2006.01) | |
| *B01J 37/04* | (2006.01) | |
| *B01J 37/08* | (2006.01) | |
| *B01J 23/888* | (2006.01) | |
| *C07B 33/00* | (2006.01) | |
| *C07C 45/35* | (2006.01) | |
| *C07C 51/25* | (2006.01) | |

(52) U.S. Cl.
CPC .............. *B01J 27/228* (2013.01); *B01J 23/002* (2013.01); *B01J 23/8876* (2013.01); *B01J 23/8885* (2013.01); *B01J 35/023* (2013.01); *B01J 35/026* (2013.01); *B01J 35/06* (2013.01); *B01J 37/0036* (2013.01); *B01J 37/038* (2013.01); *B01J 37/04* (2013.01); *B01J 37/088* (2013.01); *C07B 33/00* (2013.01); *C07C 45/35* (2013.01); *C07C 51/252* (2013.01); *B01J 2523/00* (2013.01)

(58) Field of Classification Search
None
See application file for complete search history.

(56) References Cited

U.S. PATENT DOCUMENTS

| | | | |
|---|---|---|---|
| 4,564,607 A | 1/1986 | Yoneda et al. | |
| 5,532,199 A * | 7/1996 | Watanabe et al. | 502/311 |
| 6,429,332 B1 * | 8/2002 | Tanimoto et al. | 562/532 |
| 6,784,134 B2 * | 8/2004 | Kasuga et al. | 502/182 |
| 2002/0198103 A1 | 12/2002 | Kasuga et al. | |
| 2003/0109381 A1 | 6/2003 | Ohishi et al. | |
| 2004/0199008 A1 | 10/2004 | Kasuga et al. | |

FOREIGN PATENT DOCUMENTS

| | | |
|---|---|---|
| JP | 59-173140 | 10/1984 |
| JP | 6-381 | 1/1994 |
| JP | 9-52053 | 2/1997 |
| JP | 2002-273229 | 9/2002 |
| JP | 2004-82099 | 3/2004 |
| JP | 2010-201401 | 9/2010 |

OTHER PUBLICATIONS

International Search Report issued Dec. 6, 2011 in International (PCT) Application No. PCT/JP2011/070348.
International Preliminary Report on Patentability and Written Opinion issued Apr. 16, 2013 in International (PCT) Application No. PCT/JP2011/070348.
Extended European Search Report issued Nov. 20, 2014 in corresponding European Patent Application No. 11825044.8.

* cited by examiner

*Primary Examiner* — Melvin C Mayes
*Assistant Examiner* — Colette Nguyen
(74) *Attorney, Agent, or Firm* — Wenderoth, Lind & Ponack, L.L.P.

(57) ABSTRACT

Provided is a catalyst for production of unsaturated aldehyde and/or unsaturated carboxylic acid, which shows excellent mechanical strength and low attrition loss and is capable of producing the object product(s) at a high yield. The catalyst comprises a catalytically active component containing molybdenum, bismuth and iron as the essential ingredients, and inorganic fibers, and is characterized in that the inorganic fibers contain at least an inorganic fiber having an average diameter of at least 8 μm and another inorganic fiber having an average diameter not more than 6 μm.

2 Claims, No Drawings

CATALYST FOR PRODUCING UNSATURATED ALDEHYDE AND/OR UNSATURATED CARBOXYLIC ACID, AND PROCESS FOR PRODUCING UNSATURATED ALDEHYDE AND/OR UNSATURATED CARBOXYLIC ACID USING THE CATALYST

TECHNICAL FIELD

This invention relates to a catalyst for producing unsaturated aldehyde and/or unsaturated carboxylic acid. More specifically, the invention relates to a catalyst suitable for production by catalytic vapor-phase oxidation of propylene, isobutylene or tertiary butyl alcohol (TBA) in the presence of molecular oxygen, of respectively corresponding unsaturated aldehyde and/or unsaturated carboxylic acid. The invention also relates to a process for producing these unsaturated aldehyde and/or unsaturated carboxylic acid using the catalyst.

BACKGROUND ART

Many proposals were made in the past, for the purpose of improving mechanical strength of catalyst, in respect of those catalysts used in production of acrolein and/or acrylic acid by catalytic vapor-phase oxidation of propylene in the presence of molecular oxygen or those used in production of methacrolein and/or methacrylic acid by catalytic vapor-phase oxidation of isobutylene or TBA.

Those proposals include, for example, a supported catalyst in which whiskers having an average diameter of not more than 1 µm are used as a carrier assistant (cf. JP 59 (1984)-173140A); a supported catalyst comprising molybdenum and bismuth as the essential ingredients, in which inorganic fibers having an average diameter of 2-200 µm are used as a carrier assistant (cf. JP 06 (1994)-381A); a ring-formed catalyst comprising molybdenum and bismuth as the essential ingredients, which also contains inorganic fibers (cf. JP 2002-273229 A); and a method of packing solid catalysts differing in mechanical strength, by dropping them by the order of their mechanical strengths from high to low, in which the amount of inorganic reinforcing agent such as inorganic fibers or whiskers is adjusted as one of the means for obtaining a catalyst of high mechanical strength (cf. JP 2004-82099A).

SUMMARY OF THE INVENTION

Problems to be Solved by the Invention

While all of those catalysts proposed as above show mechanical strength improved by a certain extent, their effects are not yet fully satisfactory, and a catalyst having still higher mechanical strength and enabling production of object product at a high yield is in demand. Moreover, those catalysts referred to in the above invariably aim at improving their mechanical strength to prevent breaking or chipping of the catalysts themselves or separation of catalytic components due to the impact incurred by drop-packing of the catalysts, no estimation being given about whittling and powdering of the catalyst surfaces by their mutual contact in such occasions in the course of their preparation as canning, transportation or packing, or by friction between the catalyst and wall surfaces. (Such powdering rate is hereafter referred to as "attrition loss".) Control of the attrition loss is very important, in consideration of the economical problem that the resulting catalyst powder brings about an increase in pressure loss and loss of catalytically active component, health problem that the workers are exposed to the catalyst powder which flies about during the catalyst packing operation, and the environmental problem that such catalyst powder is scattered into the air.

The object of the present invention is to solve the above problems in the conventional technology and to provide a catalyst suitable for catalytic vapor-phase oxidation of propylene, isobutylene or TBA using molecular oxygen to produce respectively corresponding unsaturated aldehyde and/or unsaturated carboxylic acid; more specifically a catalyst excelling in mechanical strength and attrition loss, which also is capable of producing the object product at a high yield.

Means for Solving the Problem

We have engaged in concentrative studies of molybdenum-bismuth type catalysts for catalytic vapor-phase oxidation of propylene, isobutylene or TBA using molecular oxygen to produce respectively corresponding unsaturated aldehyde and/or unsaturated carboxylic acid, with the view to improve their mechanical strength and control their attrition loss, to now discover that not only the mechanical strength but also the attrition loss of the catalyst can be improved by having it contain, besides the catalytically active component, at least two kinds of inorganic fibers differing in average diameter, and moreover that the catalyst is capable of producing the object product at a high yield. More specifically, we have discovered that a catalyst comprising molybdenum, bismuth and iron as the essential catalytically active ingredients and inorganic fibers, said inorganic fibers comprising at least one inorganic fiber having an average diameter of at least 8 µm and another inorganic fiber having an average diameter not more than 6 µm, shows excellent mechanical strength and low attrition loss, and can produce the object product at a high yield.

We have also discovered that the detrimental effect of the inorganic fibers on the catalytic performance could be suppressed by setting the total content of the inorganic fibers to be from 0.5 to 30 mass % to the catalytically active component.

Effect of the Invention

Thus, according to the invention provided is a catalyst for catalytic vapor-phase oxidation of propylene, isobutylene or TBA with molecular oxygen to produce respectively corresponding unsaturated aldehyde and/or unsaturated carboxylic acid, which shows excellent mechanical strength and low attrition loss, and enables to produce the object product at a high yield.

EMBODIMENTS FOR WORKING THE INVENTION

Hereinafter a catalyst of the invention for preparation of such unsaturated aldehyde and/or unsaturated carboxylic acid, and a process for preparation of unsaturated aldehyde and/or unsaturated carboxylic acid using said catalyst are explained in details, it being understood that the scope of this invention is not restricted by the explanations and that any of the specific embodiments hereinafter exemplified can be suitably changed within the limit not impairing the purpose of this invention.

The catalyst for preparation of unsaturated aldehyde and/or unsaturated carboxylic acid according to the invention comprises a catalytically active component which contains molybdenum, bismuth and iron as the essential ingredients, and inorganic fibers, said inorganic fibers comprising at least a kind of inorganic fiber having an average diameter of at least 8 µm and another kind of inorganic fiber having an average diameter no more than 6 µm, and the catalytically active component preferably containing a complex oxide represented by the following general formula (1):

$$Mo_{12}Bi_aFe_bA_cB_dC_eD_fO_x \qquad (1)$$

(in which Mo is molybdenum; Bi is bismuth; Fe is iron; A is at least one element selected from cobalt and nickel; B is at least one element selected from alkali metal, alkaline earth metal and thallium; C is at least one element selected from tungsten, silicon, aluminum, zirconium and titanium; D is at least one element selected from phosphorus, tellurium, antimony, tin, cerium, lead, niobium, manganese, arsenic, boron and zinc; and O is oxygen; a, b, c, d, e, f and x stand for the respective atomic ratios of Bi, Fe, A, B, C, D and O, where $0<a\leq10$, $0<b\leq20$, $2\leq c\leq20$, $0<d\leq10$, $0\leq e\leq30$, $0\leq f\leq4$, and x is a numeral value determined by the oxidized state of each of the elements).

The catalyst of the present invention must contain, concurrently with above catalytically active component, at least a kind of inorganic fiber having an average diameter of at least 8 µm, preferably at least 10 µm, and another kind of inorganic fiber having an average diameter not more than 6 µm, preferably not more than 3 µm. The inorganic fiber having an average diameter of at least 8 µm, preferably at least 10 µm, effectively works for improving mechanical strength of the catalyst in main, such as prevention of breaking or chipping, because of its big size. On the other hand, the inorganic fiber having an average diameter not more than 6 µm, preferably not more than 3 µm, is thought to work mainly for improving the attrition loss such that it keeps back the powder at the catalyst surface, because of its fine size. In the present invention, it is important that the catalyst contains at least two kinds of inorganic fibers differing in average diameter. With either of one kind of the fibers alone, it is difficult to simultaneously improve both the mechanical strength and attrition loss, and in consequence the mechanical strength or attrition loss left out unimproved comes to adversely affect the catalyst's performance.

The inorganic fibers to be used in the invention are not particularly limited by their constituent material and, for example, glass fiber, ceramic fiber, metal fiber, mineral fiber, carbon fiber, various whiskers and the like can be used. Their crystalline structure may be either polycrystalline or monocrystalline. Said "at least two kinds of inorganic fibers" may be of a same material or of different materials, which can be suitably selected so long as their average diameters meet the above requirements.

According to the invention, average length of the inorganic fibers is not particularly limited. Whereas, in consideration of their dispersibility in the catalyst, it is preferably within a range of from 1 µm to 1,000 µm, in particular, from 10 µm to 500 µm. Whereas, even such an inorganic fiber having an average length exceeding 1,000 µm can be conveniently used, when it is cut to have an average length falling within the range of from 10 µm to 1,000 µm, by a powerful agitation with a homogenizing mixer or the like.

Respective contents of those at least two kinds of inorganic fibers are suitably within a range of from 0.5 to 20 mass % each to the total catalytically active component, in view of their improving effect on the mechanical strength and/or attrition loss and catalytic performance, in particular, the catalyst life. The total content of the inorganic fibers preferably lies between 0.5 and 30 mass %, to the mass of catalytically active component. When it is less than the above-specified range, the improvement in mechanical strength and/or attrition loss is insufficient, and when it exceeds the above range, the amount of catalytically active component in the catalyst becomes relatively less, which shortens the catalyst life. Moreover, the ratio between the contents of an inorganic fiber having an average diameter of at least 8 µm and that having an average diameter not more than 6 µm preferably is from 1:0.2 to 1:5 on mass basis, considering that an excessive increase in either one of them results in insufficient effect of the other inorganic fiber(s).

The catalyst according to the present invention can be prepared following processes used in general for preparation of known catalysts for producing unsaturated aldehyde and/or unsaturated carboxylic acid, except that the catalyst must contain at least an inorganic fiber having an average diameter of at least 8 µm and another inorganic fiber having an average diameter not more than 6 µm, for example, by the steps as follows.

First, oxide(s), hydroxide(s), ammonium salt(s), nitrate(s), carbonate(s), sulfate(s), organic acid salt(s) or the like of each of the ingredient elements, or their aqueous solutions or sols, or compound(s) containing plural elements, are made into an aqueous solution or aqueous slurry, which serves as the starting material of the catalytically active component represented by the general formula (1) (which may hereafter be referred to as "starting material liquid mixture") by, for example, mixing them with water.

The resulting starting material liquid mixture then is dried by various means such as heating or pressure reduction, where necessary, to prepare a catalyst precursor. For drying by heating, for example, such methods can be optionally used as forming a powdery catalyst precursor with spray dryer, drum dryer or the like; making block-formed or flaky catalyst precursor using a box-type dryer or tunnel-type dryer by heating in an inert gas such as air or nitrogen, or in a gaseous current of, for example, nitrogen oxide or the like; or condensing the starting material liquid mixture once, evaporation drying the same to form solid cakes and further heat-treating the solid product as above. The heating temperature ranges from 80 to 300° C., preferably from 130 to 250° C., and the heating time preferably ranges from 1 to 20 hours. As the drying means by pressure reduction, for example, a vacuum dryer can be used, whereby to produce a block-formed or powdery catalyst precursor. The dry products obtained by above-described methods can be calcined at 350-600° C., preferably 400-550° C., inter alia, 420-500° C. for 1-10 hours in an atmosphere of molecular oxygen-containing gas such as air. So obtained calcination product may also be used as the catalyst precursor. Furthermore, a mixture of above dry product with the calcination product can be used as the catalyst precursor.

Thus obtained catalyst precursor (the dry product, calcination product or a mixture thereof) is sent to a molding step, after a grinding step or classification step to provide a powder of a suitable fineness, where necessary. While the fineness of powder is not particularly limited, one not more than 500 µm is preferred in respect of good moldability.

The molding methods include those of imparting to the catalyst precursor or a mixture of the catalyst precursor with a powdered inert substance a fixed shape by extrusion molding, tabletting and the like, or those of having an optional inert carrier of a fixed shape support the catalyst precursor or a mixture of the catalyst precursor with a powdered inert substance thereon. For the purpose of increasing the selectivity and yield of the object product, it is necessary to suppress successive reactions, and for the suppression, less thickness of the catalytically active component is preferred. In this regard, the latter case of having an inert carrier support the component is preferred as the molding method.

The method of adding the inorganic fibers is subject to no particular limitation, and any can be used so long as it can uniformly disperse the inorganic fibers in the catalytically active component. For example, the fibers may be added to the starting material liquid mixture of the catalytically active component represented by the general formula (1), or to the catalyst precursor obtained by drying or calcining the starting material liquid mixture of the catalytically active component. In the latter case, the catalyst precursor and the inorganic fibers may be mixed in powder particulate condition or the inorganic fibers may be added to a liquid dispersion of the catalyst precursor in a solvent (e.g., water) and mixed together. Of those methods, one of adding the inorganic fibers to starting material liquid mixture of the catalytically active component is preferred, in regard to dispersibility of the inorganic fibers. The inorganic fibers may be added in a lump or in portions, for example, in such a manner that a part thereof is added to the starting material liquid mixture, and the remainder, to the catalyst precursor which is obtained by drying or calcining the liquid mixture.

In case of extrusion molding or tabletting, the shape of the molded bodies is subject to no particular limitation, which may be spherical, cylindrical, ring-formed or irregular. Needless to say, it is unnecessary for the spherical bodies to be true spheres, but substantial spheres are satisfactory. Similarly, cylindrical or ring-formed shapes need not to have a true circular cross-section, substantially circular cross-section being satisfactory. As to the spherical catalyst or pelletized (cylindrical or ring-formed) catalysts, their diameter D and length L are preferably both from 3 to 15 mm, in particular, from 3 to 10 mm, although not limited thereto. In the pelletized catalysts, particularly their length L preferably is from 0.5 to 2.0 times of their diameter D, more preferably from 0.7 to 1.5 times. As to the ring-formed catalyst, one having a through-hole of an inner diameter from 0.1 to 0.7 time of their outer diameter in the vertical direction is preferred.

As the supporting method, the one as described in, for example, JP 49 (1974)-11371B in which the starting material liquid mixture is deposited on an inert carrier having a fixed shape, by heating and vaporizing the liquid material under stirring, the one as described in JP 59 (1984)-173140A or JP 6 (1994)-381A in which a slurry of the starting material liquid mixture is deposited on an inert carrier, at the same time evaporating the solvent to effect the supporting, the one as described in JP 63 (1988)-200839A, JP 10 (1998)-28877A or JP 2004-136267A, in which a catalyst precursor as earlier described is supported in powder form on an inert carrier, or the like can be used.

Examples of the inert carrier include alumina, silica, silica-alumina, titania, magnesia, steatite, cordierite, silica-magnesia, silicon carbide, silicon nitride and zeolite. Their shape is subject to no particular limitation, any known shape such as spherical, cylindrical, ring-formed and the like being useful. The ratio of the supported amount of the catalytically active component to the inert carrier again is not particularly limited, while a range from 20 to 300 mass %, in particular, from 50 to 200 mass %, is preferred.

In the molding step, a molding promoter or binder for improving moldability, a pore-forming agent for forming adequate pores in the catalyst, and the like may be used, examples of which include organic compounds such as ethylene glycol, glycerin, propionic acid, maleic acid, benzyl alcohol, propyl alcohol, butyl alcohol and phenols; and inorganic compounds such as water, nitric acid, ammonium nitrate and ammonium carbonate.

The molded bodies or catalyst-carrying bodies as obtained in the above molding step are sent to the subsequent drying step and/or calcination step.

In the drying step, the molded bodies or catalyst-carrying bodies are dried in a box-type dryer, tunnel-type dryer or the like which have been in general use, by heating in an inert gas such as air or nitrogen, or in a gaseous current of other substance such as nitrogen oxide. The drying temperature ranges from 80 to 300° C., preferably from 130 to 250° C., and the drying time preferably ranges from 1 to 20 hours.

A calcining oven to be used in the calcination step again is subject to no particular limitation, and any of generally used box-type calcination oven, tunnel-type calcination oven and the like may be used. The calcination temperature ranges from 350 to 600° C., preferably from 400 to 550° C., inter alia, from 420 to 500° C., and the calcination time preferably ranges from 1 to 10 hours. Any oxidizing atmosphere can be used for the calcination, a molecular oxygen-containing gaseous atmosphere being preferred. Hence, the calcination step is preferably conducted while passing a molecular oxygen-containing gas. As such molecular oxygen-containing gas, air is conveniently used.

The calcination is usually conducted after aforesaid drying step, while the drying step may be omitted. Furthermore, those molded bodies or catalyst-carrying bodies prepared with already calcined catalytically active component as a catalyst precursor do not necessarily require the calcination step but aforesaid drying step alone will suffice, provided the molding promoter or binder which were used in the molding step can be eliminated.

While there is no particular limitation for the reactor to be used in the process of the invention for producing from propylene, isobutylene or TBA respectively corresponding unsaturated aldehyde and/or unsaturated carboxylic acid, by catalytic vapor-phase oxidation using molecular oxygen, except that it should be a fixed bed reactor, a fixed bed shell-and-tube reactor is particularly preferred, the inner diameter of a reaction tube therein being usually from 15 to 50 mm, preferably from 20 to 40 mm, inter alia from 22 to 38 mm.

It is not necessarily required to pack each reaction tube in a 1 to shell-and-tube reactor with one, single catalyst, it being permissible to pack it in such a manner that known plural catalysts shall form layers in the tube (each layer may hereafter be referred to as "a reaction zone"). For example, a method of packing plural catalysts differing in occupying capacity in a tube in such a manner that the catalyst-occupying capacity lessens from the entrance side of a starting gas toward its exit side (cf. JP 4 (1992)-217932A); or a method of packing plural catalysts differing in catalyst-supporting ratio in such a manner that the supporting ratio increases from the entrance side of a starting gas toward the exit side (cf. JP 10 (1998)-168003A); or a method comprising diluting a part of the catalyst with an inert carrier or the like (cf. JP 2005-320315A); or a method using the above-described features in combination, may be used. In such an occasion, the number of reaction zones is suitably selected according to the reaction conditions or scale of the reactor in individual case. Whereas, too many reaction zones give rise to a problem of rendering the catalyst-packing operations complex, and industrially from 2 to up to around 6 is desirable.

The reaction conditions in the invention are free from any particular restriction, and any of conditions generally used in this type of reactions may be adopted. For example, the reaction can be performed by contacting a feedstock gas which is a mixture of 1-15 vol %, preferably 4-12 vol %, of propylene, isobutylene or TBA; 0.5-25 vol %, preferably 2-20 vol % of molecular oxygen; 0-30 vol %, preferably 0-25 vol % of steam; and balance vol % of an inert gas (e.g., nitrogen gas), with the catalyst at a temperature of 250-450° C., under a pressure of 0.1-1.0 MPa and at a space velocity of 300-5,000 hr$^{-1}$ (STP).

The grade of the feedstock gas for the reaction is free from any particular restriction. For example, when propylene is used as the feedstock gas, propylene of polymer grade or chemical grade can be used. Also a gaseous mixture containing propylene, which is obtained from (oxidative) dehydrogenation reaction of propane, or the gaseous mixture to which air or oxygen and the like are added, where necessary, can also be used.

EXAMPLES

Hereinafter the invention is explained more specifically, referring to working Examples, it being understood that the invention is in no way limited thereby. In the following, "mass part" may be simply given as "part" for convenience. The conversions and yields in the Examples and Comparative Examples are calculated by the following equations:

$$\text{Conversion [mol \%]} = \frac{\text{(Mol number of reacted starting material)}}{\text{(Mol number of fed starting material)}} \times 100$$

Yield [mol %] =

$$\frac{\begin{array}{c}\text{(Total mol number of unsaturated aldehyde formed}\\ \text{and unsaturated carboxylic acid formed)}\end{array}}{\text{(Mol number of fed starting material)}} \times 100$$

[Measurement of the Catalyst's Mechanical Strength]

A stainless steel reaction pipe having an inner diameter of 25 mm and a length of 5000 mm was vertically set, and its lower end was sealed with a 1 mm-thick stainless steel receiver plate. About 50 g of a catalyst was weighed and dropped into the reaction pipe from the upper end of the pipe. Then the stainless steel receiver plate at the lower end of the reaction pipe was detached, to gently take out the catalyst from the reaction pipe. The catalyst so taken out was sifted with a sieve of a mesh size covering from 50 to 90% of the shorter of the standard diameter or length set for the catalyst grain and the mass (g) of the catalyst remaining on the sieve was weighed.

Mechanical strength (mass %) =

$$\frac{\text{(Mass(g) of catalyst remaining on the sieve)}}{\text{(Mass(g) of catalyst dropped from upper end of reaction pipe)}} \times 100$$

[Measurement of the Catalyst's Attrition Loss]

About 200 g of a catalyst was weighed and fed into a cylindrical drum-formed stainless steel air-tight vessel having a circular cross-section of 150 mm in diameter in the perpendicular direction and a horizontal width of 150 mm. The vessel was rotated centering around its horizontal center axis at 150 rpm for 30 minutes. Thereafter the catalyst was taken out and sifted with a sieve of a mesh size covering from 10 to 50% of the shorter of the standard diameter or length set for the catalyst grains and the mass (g) of the catalyst remaining on the sieve was weighed.

$$\text{Attrition loss (mass \%)} = \frac{\begin{array}{c}\text{(Mass(g) of catalyst fed into vessel)} -\\ \text{(Mass(g) of catalyst remaining on sieve)}\end{array}}{\text{Mass(g) of catalyst fed into vessel]}} \times 100$$

Example 1

[Catalyst Preparation]

In 4,000 parts of distilled water, 1,000 parts of ammonium paramolybdate and 3.3 parts of potassium nitrate were dissolved, and to the solution 284 parts of 20 mass % silica sol was added (Liquid A). Separately, 50 parts of 65 wt % nitric acid was added to 600 parts of distilled water, and in which 298 parts of bismuth nitrate, 689 parts of cobalt nitrate and 210 parts of iron nitrate were dissolved (Liquid B). So obtained Liquid A and Liquid B were mixed, and into the mixture 193 parts of alumina and 54.7 parts of tungsten oxide were added, followed by 30 minutes' continuous stirring. Then a glass fiber having an average diameter of 6 μm and an average length of 90 μm, and another glass fiber having an average diameter of 8 μm and an average length of 150 μm were added, each in an amount corresponding to 15 mass % to the catalytically active component, followed by further 120 minutes' continuous stirring. Thus obtained slurry was heated under stirring and solidified into a cake. The resulting solid body was dried for about 5 hours at 200° C. under an atmosphere of air. After the drying, the solid body was pulverized to no greater than 500 μm to provide a catalyst precursor. To the catalyst precursor, pure water was added as a binder and kneaded together. Thus kneaded product was extrusion-molded into rings of each 6.5 mm in outer diameter, 2 mm in inner diameter and 6.5 mm in height, which were calcined at 470° C. for 6 hours in an atmosphere of air to provide Catalyst 1. The composition of metal elements of this Catalyst 1 excluding oxygen was as follows:

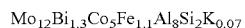

Catalyst 1

The mechanical strength of this Catalyst 1 was measured using a 5 mm-mesh sieve, and its attrition loss, using a 2 mm-mesh sieve. The mechanical strength and attrition loss of Catalyst 1 were as shown in Table 1.

[Reactor]

A reactor formed of a steel reaction tube of 3,000 mm in total length and 25 mm in inner diameter, and a shell covering the reaction tube for passing a heating medium was installed in vertical direction. Catalyst 1 was dropped thereinto from an upper part of the tube to pack the latter up to the layer length of 2,800 mm.

<Oxidation Reaction>

From a lower part of the Catalyst 1-packed reaction tube, a feedstock gas, which was a mixture of 7.0 vol % of propylene, 13 vol % of oxygen, 6 vol % of steam and the balance vol % of nitrogen, was introduced at a space velocity of 1450 hr$^{-1}$ (STP), to carry out the catalytic vapor-phase oxidation of propylene. In that occasion, the temperature of the heating medium (the reaction temperature) was adjusted to make the propylene conversion about 97 mol %. The results were as shown in Table 2.

Comparative Example 1

Example 1 was repeated except that the glass fiber having an average diameter of 6 μm and an average length of 90 μm was not added, to provide Catalyst 2. The composition of metal elements of this Catalyst 2 excluding oxygen was the same to that in Example 1. The mechanical strength and attrition loss of Catalyst 2 were as shown in Table 1. This Catalyst 2 was packed in the reactor in the manner similar to Example 1, and the oxidation was conducted under identical conditions. The results were as given in Table 2.

Comparative Example 2

Example 1 was repeated except that 15 mass % to the catalytically active component of the glass fiber having an average diameter of 6 µm and an average length of 90 µm was replaced with mass % to the catalytically active component of a silica-alumina fiber having an average diameter of 3 µm and an average length of 50 µm; and that the glass fiber having an average diameter of 8 µm and an average length of 150 µm was not added, to provide Catalyst 3. The composition of metal elements of this Catalyst 3 excluding oxygen was the same to that in Example 1. The mechanical strength and attrition loss of Catalyst 3 were as shown in Table 1. This Catalyst 3 was packed in the reactor in the manner similar to Example 1, and the oxidation was conducted under identical conditions. The results were as given in Table 2.

Example 2

[Catalyst Preparation]

In 4,000 parts of distilled water, 1,000 parts of ammonium paramolybdate and 3.8 parts of potassium nitrate were dissolved (Liquid A). Separately, 50 parts of 65 wt % nitric acid was added to 800 parts of distilled water, and in which 252 parts of bismuth nitrate, 962 parts of cobalt nitrate, 229 parts of iron nitrate and 275 parts of nickel nitrate were dissolved (Liquid B). Thus obtained Liquid A and Liquid B were mixed, and to which 120 parts of alumina was added, followed by continuous 60 minutes' stirring. The resulting slurry was heated under stirring until it solidified to a cake. The solid body was dried at 200° C. for about 5 hours under an atmosphere of air. So dried solid body was pulverized to no greater than 500 µm in size to provide a catalyst precursor. To the catalyst precursor, a glass fiber having an average diameter of 6 µm and an average length of 90 µm was added in an amount of 5 mass % to the catalytically active component, and also a glass fiber having an average diameter of 10 µm and an average length of 300 µm was added in an amount of 10 mass % to the catalytically active component, to form a powder mixture. Into a tumbling granulation machine, 1,000 parts of spherical alumina carrier having an average grain size of 5.2 mm was thrown, and then the catalyst powder was slowly thrown into the machine, together with 10 mass % of aqueous ammonium nitrate solution serving as a binder, to have the carrier support the catalyst thereon, followed by 6 hours' calcination at 470° C. in an atmosphere of air, to provide Catalyst 4. This Catalyst 4 had a catalyst-supporting ratio of about 120 mass %, and the composition of metal elements therein excluding the carrier and oxygen was as follows:

$$Mo_{12}Bi_{1.1}Co_7Fe_{1.2}Ni_2Al_5K_{0.08} \qquad \text{Catalyst 4}$$

The supporting ratio was determined following the equation below:

Supporting ratio [mass %] =

$$\frac{\text{Mass of supported catalytically active component}}{\text{Mass of carrier used}} \times 100.$$

The mechanical strength of this Catalyst 4 was measured with a sieve of 5 mm-mesh, and the attrition loss, with a sieve of 2 mm-mesh. The mechanical strength and attrition loss of this Catalyst 4 were as shown in Table 1.

This Catalyst 4 was packed in the reactor in the manner similar to Example 1, and the oxidation was conducted under identical conditions. The results were as given in Table 2.

Example 3

[Catalyst Preparation]

In 4,000 parts of distilled water, 1,000 parts of ammonium paramolybdate and 3.8 parts of potassium nitrate were dissolved (Liquid A). Separately, 50 parts of 65 wt % nitric acid was added to 800 parts of distilled water, and in which 412 parts of bismuth nitrate, 824 parts of cobalt nitrate and 191 parts of iron nitrate were dissolved (Liquid B). So obtained Liquid A and Liquid B were mixed, to which 96.3 parts of alumina and 109 parts of tungsten oxide were added, followed by continuous 30 minutes' stirring. Then a silica-alumina fiber having an average diameter of 4 µm and an average length of 70 µm was added in an amount of 5 mass % to the catalytically active component, and also a glass fiber having an average diameter of 10 µm and an average length of 300 µm was added in an amount of 10 mass % to the catalytically active component, followed by further continuous stirring for 120 minutes. The resulting slurry was heated under stirring until a solid cake was formed. The solid body was dried at 200° C. for about 5 hours in an atmosphere of air. The dried solid body was pulverized to not greater than 500 µm in size, to provide a catalyst precursor. Into a tumbling granulation machine, 1,100 parts of spherical alumina carrier having an average grain size of 5.2 mm was thrown, and then the catalyst powder was slowly thrown into the machine, together with 15 mass % of aqueous ammonium nitrate solution serving as a binder, to have the carrier support the catalyst thereon, followed by 6 hours' calcination at 470° C. in an atmosphere of air, to provide Catalyst 5. This Catalyst 5 had a catalyst-supporting ratio of about 120 mass %, and the composition of metal elements therein excluding the carrier and oxygen was as follows:

$$Mo_{12}Bi_{1.8}Co_6Fe_1Al_4W_1K_{0.08} \qquad \text{Catalyst 5}$$

The mechanical strength of this Catalyst 5 was measured with a sieve of 5 mm-mesh, and the attrition loss, with a sieve of 2 mm-mesh. The mechanical strength and attrition loss of this Catalyst 5 were as shown in Table 1.

This Catalyst 5 was packed in the reactor in the manner similar to Example 1, and the oxidation was conducted under identical conditions. The results were as given in Table 2.

Comparative Example 3

Example 3 was repeated except that 5 mass % to the catalytically active component of the silica-alumina fiber of 4 µm in average diameter and 70 µm in average length was replaced with 5 mass % to the catalytically active component of a glass fiber of 8 µm in average diameter and 150 µm in average length, to provide Catalyst 6. The composition of metal elements of this Catalyst 6 excluding oxygen was the same to that in Example 3. The mechanical strength and attrition loss of Catalyst 6 were as given in Table 1. This Catalyst 6 was packed in the reactor in the manner similar to Example 1, and the oxidation was conducted under identical conditions. The results were as given in Table 2.

Example 4

Example 3 was repeated except that 5 mass % to the catalytically active component of the silica-alumina fiber of 4 µm in average diameter and 70 μm in average length was replaced with 10 mass % to the catalytically active component of a SiC whisker of 0.6 μm in average diameter and 30 μm in average length, and that 10 mass % to the catalytically active component of the glass fiber of 10 μm in average diameter and 300 μm in average length was replaced with 5 mass % to the catalytically active component of a glass fiber of 20 μm in average diameter and 500 μm in average length, to provide Catalyst 7. The composition of metal elements of this Catalyst 7 excluding oxygen was the same to that in Example 3. The mechanical strength and attrition loss of Catalyst 7 were as given in Table 1. This Catalyst 7 was packed in the reactor in the manner similar to Example 1, and the oxidation was conducted under identical conditions. The results were as given in Table 2.

Example 5

Example 3 was repeated except that 5 mass % to the catalytically active component of the silica-alumina fiber of 4 μm in average diameter and 70 μm in average length was replaced with 5 mass % to the catalytically active component of a silica-alumina fiber of 3 μm in average diameter and 50 μm in average length, and that 10 mass % to the catalytically active component of the glass fiber of 10 μm in average diameter and 300 μm in average length was replaced with 5 mass % to the catalytically active component of a glass fiber of 15 μm in average diameter and 350 μm in average length, to provide Catalyst 8. The composition of metal elements of this Catalyst 8 excluding oxygen was the same to that in Example 3. The mechanical strength and attrition loss of Catalyst 8 were as given in Table 1. This Catalyst 8 was packed in the reactor in the manner similar to Example 1, and the oxidation was conducted under identical conditions. The results were as given in Table 2.

TABLE 2

| | Catalyst No. | Reaction Temp. (° C.) | Propylene Conversion (mol %) | Acrolein + Acrylic Acid Selectivity (mol %) | Acrolein + Acrylic Acid Yield (mol %) |
|---|---|---|---|---|---|
| Example 1 | Catalyst 1 | 314 | 97.0 | 93.7 | 90.9 |
| Comparative Example 1 | Catalyst 2 | 324 | 97.0 | 92.1 | 89.3 |
| Comparative Example 2 | Catalyst 3 | 318 | 97.0 | 92.3 | 89.5 |
| Example 2 | Catalyst 4 | 313 | 97.1 | 94.1 | 91.4 |
| Example 3 | Catalyst 5 | 310 | 97.0 | 94.4 | 91.6 |
| Comparative Example 3 | Catalyst 6 | 316 | 97.1 | 92.6 | 89.9 |
| Example 4 | Catalyst 7 | 310 | 97.1 | 94.8 | 92.1 |
| Example 5 | Catalyst 8 | 311 | 97.0 | 94.9 | 92.1 |

The invention claimed is:

1. A catalyst for preparation of unsaturated aldehyde and/or unsaturated carboxylic acid, comprising a catalytically active component and inorganic fibers,
   wherein said catalytically active component comprises molybdenum, bismuth and iron as essential ingredients,
   wherein said inorganic fibers comprises two kinds of fibers having different average diameters in which one is an inorganic fiber having an average diameter of at least 8 μm and another is an inorganic fiber having an average diameter not more than 6 μm,
   wherein the ratio between the content of the inorganic fiber having an average diameter of at least 8 μm and the content of the inorganic fiber having an average diameter not more than 6 μm is from 1:0.2 to 1:5 on a mass basis,
   wherein the total content of the inorganic fibers is from 0.5 to 30 mass % relative to the catalytically active component,
   wherein the catalytically active component and the inorganic fibers are supported on an inert carrier, and
   wherein the catalytically active component is a complex oxide represented by the following general formula (1):

TABLE 1

| | Catalyst No. | Inorganic Fiber-1 | | | | Inorganic Fiber-2 | | | | Mechanical Strength (mass %) | Attrition loss (mass %) |
| | | material | diameter (μm) | length (μm) | content (mass %) | material | diameter (μm) | length (μm) | content (mass %) | | |
|---|---|---|---|---|---|---|---|---|---|---|---|
| Example 1 | Catalyst 1 | glass | 6 | 90 | 15 | glass | 8 | 150 | 15 | 98.2 | 6.2 |
| Comparative Example 1 | Catalyst 2 | — | — | — | — | glass | 8 | 150 | 15 | 97.4 | 20.8 |
| Comparative Example 2 | Catalyst 3 | silica-alumina | 3 | 50 | 15 | — | — | — | — | 85.4 | 7.2 |
| Example 2 | Catalyst 4 | glass | 6 | 90 | 5 | glass | 10 | 300 | 10 | 98.7 | 5.5 |
| Example 3 | Catalyst 5 | silica-alumina | 4 | 70 | 5 | glass | 10 | 300 | 10 | 99.5 | 4.7 |
| Comparative Example 3 | Catalyst 6 | glass | 8 | 150 | 5 | glass | 10 | 300 | 10 | 99.3 | 19.3 |
| Example 4 | Catalyst 7 | SiC whisker | 0.6 | 30 | 10 | glass | 20 | 500 | 5 | 99.7 | 3.4 |
| Example 5 | Catalyst 8 | silica-alumina | 3 | 50 | 5 | glass | 15 | 350 | 5 | 99.5 | 3.5 |

$$Mo_{12}Bi_aFe_bA_cB_dC_eD_fO_x \quad (1)$$

wherein Mo is molybdenum; Bi is bismuth; Fe is iron; A is at least one element selected from the group consisting of cobalt and nickel; B is at least one element selected from the group consisting of alkali metal, alkaline earth metal and thallium; C is at least one element selected from the group consisting of tungsten, silicon, aluminum, zirconium and titanium; D is at least one element selected from the group consisting of phosphorus, tellurium, antimony, tin, cerium, lead, niobium, manganese, arsenic, boron and zinc; and O is oxygen;

wherein a, b, c, d, e, f and x stand for the respective atomic ratios of Bi, Fe, A, B, C, D and O; and wherein $0 < a \leq 10$, $0 < b \leq 20$, $2 \leq c \leq 20$, $0 < d \leq 10$, $0 \leq e \leq 30$, $0 \leq f \leq 4$, and x is a numeral value determined by the oxidized state of each of the elements.

2. A process for preparation of unsaturated aldehyde and/or unsaturated carboxylic acid comprising catalytic vapor-phase oxidation of propylene, isobutylene or tertiary butyl alcohol in the presence of molecular oxygen, which uses the catalyst according to claim 1.

* * * * *